US00PP08348P

United States Patent [19]

Weigle

[11] Patent Number: Plant 8,348

[45] Date of Patent: Aug. 17, 1993

[54] WEIGELA NAMED WHITE KNIGHT

[76] Inventor: Jack L. Weigle, 48 Cottage St., Fredonia, N.Y. 14063

[21] Appl. No.: 797,412

[22] Filed: Nov. 4, 1991

[51] Int. Cl.[5] ..... A01H 5/00

[52] U.S. Cl. ..... Plt./54.1

[58] Field of Search ..... Plt./54.1

*Primary Examiner*—James R. Feyrer

[57] ABSTRACT

A new and distinct Weigela cultivar particularly distinguished by profuse production of medium-sized white flowers borne on the upright stems of a tall spreading bush. This plant exhibits winter hardiness along with a mild fragrance, an unusual characteristic for Weigela.

1 Drawing Sheet

BACKGROUND OF THE NEW PLANT

My new Weigela plant originated as a hybrid seedling resulting from the crossing of the varieties, IA725543 and IA724327 (both unpatented), being grown in greenhouse and outdoors at Iowa State University, Ames, Iowa. Because of the white flower color of this plant, its winter hardiness and pleasing fragrance, I propagated this plant by means of cuttings to test its character. Because of such favorable results, propagation in this manner was carried on at Iowa State University through several successive generations. This demonstrated clearly that the novel characteristics of this plant hold true from generation to generation and appear to be firmly fixed. Therefore, its homogeneity for commercial propagation can be assured.

DESCRIPTION OF THE DRAWING

My new Weigela variety is illustrated by the accompanying photographic drawing which shows a fully developed plant with buds in several stages of development along with fully opened flowers and foliage; the color rendition being as nearly true to that herein specified as is reasonably possible to obtain by conventional photographic procedures.

DESCRIPTION OF THE NEW PLANT

The following is a detailed description of my new Weigela plant based upon observation of plants grown at Iowa State University, color designations being according to The R.H.S. Colour Chart published by The Royal Horticultural Society of London, England.

THE PLANT

Origin: Seedling.
Parentage: Unpatented.
- *Seed parent.*—IA725543.
- *Pollen parent.*—IA724327.

Classification:
- *Botanio.*—*Weigela florida.*
- *Commercial.*—Weigela.

Form: A strong spreading bush having a normal branching character.
Height: 2m.
Foilage:
- *Quantity.*—Abundant.
- *Size of leaves.*—Approximately 8–12.5 cm. long by 3–5 cm. wide.
- *Shape.*—Elliptic with serrulate margins.
- *Texture.*—Smooth.

- *Color.*—Lower side — 137-A. Upper side — 147-A.

Leaflets: About 1.8×4.5 cm.
Ribs and Veins: Primate and netted.
Petioles: About 8 mm. in length.

THE BUD

Size: Moderate.
Diameter: About 8 mm.
Length: About 2.8 cm.
Form: Long.
Color:
- *When sepals first divide.*—Naples yellow 11-B.
- *When petals begin to unfurl.*—yellow 10-C with blush of red 54-A.

Sepals:
- *Character.*—The sepals stand up when flowers open.
- *Color.*—Inside — Green 144-C. Outside — Green 135-C.

Calyx:
- *Shape.*—Pointed.
- *Size.*—About 9 mm..
- *Aspect.*—Smooth.

THE FLOWER

Blooming habit: From late May through early June, with repeat blooming possible.
Size of bloom: Medium.
- *Diameter.*—About 2½ cm.
- *Depth.*—About 3 cm.

Borne: Singly on long, strong, upright stem.
Shape:
- *When bloom first opens.*—Cup shaped.
- *When bloom matures.*—only exterior half of petal flattens.

Petalage:
- *Number of petals.*—Five.
- *Arrangement.*—Fused at base.
- *Form.*—Funnel-shaped with smooth margins.
- *Appearance.*—Satiny.
- *Color.*—Outer body — White 155-C with red 51-A at base. Reverse side — White 155-C with yellow 2A at throat.
- *Fragrance.*—Mild and pleasant.

THE REPRODUCTIVE ORGANS

Stamens:
- *Number.*—5.
- *Arrangement.*—Arranged around pistal.

*Length.*—About 2 cm.

Filaments:

*Length.*—About 3.5 cm.

*Color.*—White.

Pollen:

*Color.*—158-A

Pistals:

*Number.*—1.

*Styles.*—One per pistal, slightly longer than filaments.

*Length.*—About 1.6 cm.

Characteristics of ovaries: 2 celled and elongated.

THE FRUIT

Fertility: The fruit is dry and contains fertile seeds.

Size: Uniform and medium sized with an axial diameter of 1.4 cm. and a transverse diameter of 2 mm.

Suture: At apex covering entire fruit.

Cavity: Long, with a depth of 1 mm and a breadth of 1.2 cm.

Calyx: Pointed and open.

*Length.*—1.8 cm.

Pubescence.—Slight.

Seed cells: Long and narrow, approximately 1.2 cm. long by 1 mm. wide.

This new plant most nearly resembles the varieties Red Prince and Bristol Snowflake. However, it is distingusihed in particular by its mild fragrance and winter hardiness.

I claim:

1. The new and distinct Weigela plant, substantially as herein shown and described, characterized in particular by its profuse production of mildly-fragrant, medium sized white flowers, the plant itself being a strong, upright, spreading bush exhibiting great winter hardiness.

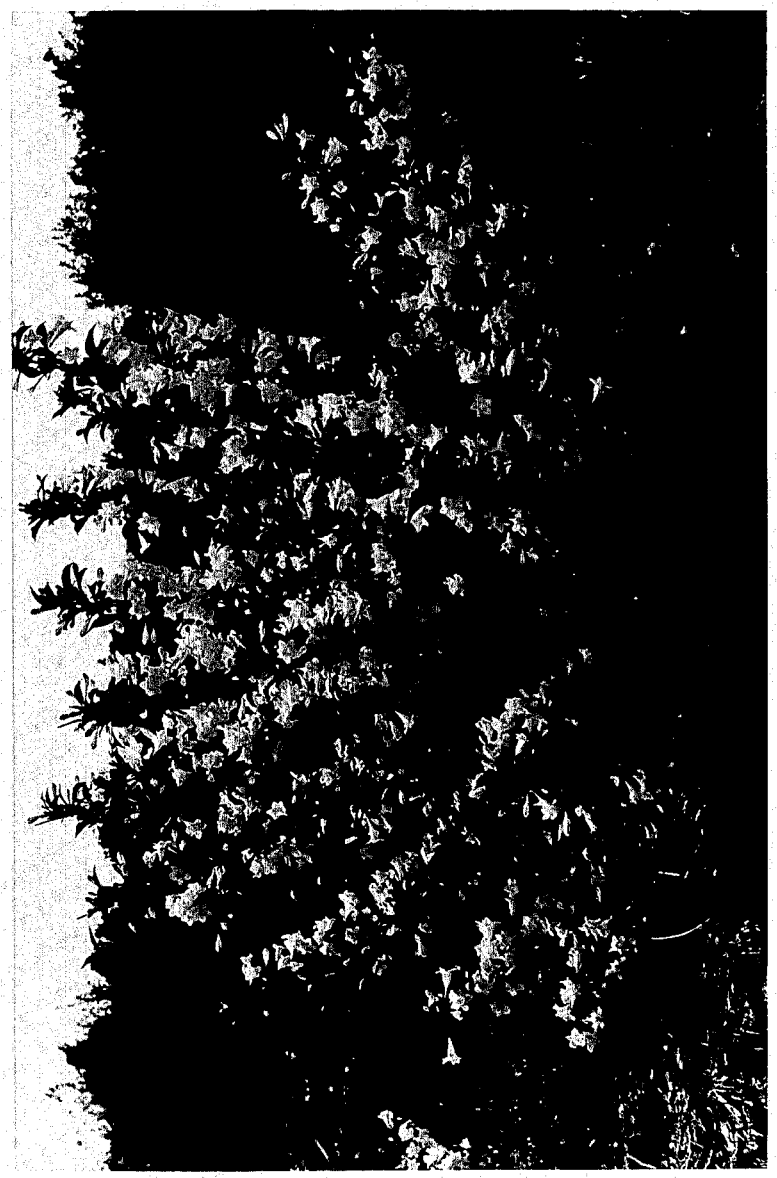

* * * * *